US011854673B2

(12) United States Patent
Are

(10) Patent No.: US 11,854,673 B2
(45) Date of Patent: *Dec. 26, 2023

(54) SYSTEMS AND METHODS FOR MANAGING CAREGIVER RESPONSIBILITY

(71) Applicant: CERNER INNOVATION, INC., Kansas City, KS (US)

(72) Inventor: Sasanka Are, Kansas City, MO (US)

(73) Assignee: CERNER INNOVATION, INC., Kansas City, MO (US)

( * ) Notice: Subject to any disclaimer, the term of this patent is extended or adjusted under 35 U.S.C. 154(b) by 886 days.

This patent is subject to a terminal disclaimer.

(21) Appl. No.: 16/235,725

(22) Filed: Dec. 28, 2018

(65) Prior Publication Data

US 2019/0206553 A1    Jul. 4, 2019

Related U.S. Application Data

(60) Provisional application No. 62/611,646, filed on Dec. 29, 2017.

(51) Int. Cl.
*G16H 40/20* (2018.01)
*G16H 10/60* (2018.01)
G16H 50/30 (2018.01)

(52) U.S. Cl.
CPC ............ *G16H 40/20* (2018.01); *G16H 10/60* (2018.01); *G16H 50/30* (2018.01)

(58) Field of Classification Search
CPC ......... G16H 40/20; G16H 10/60; G16H 50/30
See application file for complete search history.

(56) References Cited

U.S. PATENT DOCUMENTS

2012/0245948 A1* 9/2012 Nolte ................... G06Q 10/10
                                                          705/2
2012/0253836 A1* 10/2012 Nolte ................... G16H 10/20
                                                          705/2

(Continued)

FOREIGN PATENT DOCUMENTS

WO       2015/023674 A1     2/2015
WO    WO-2015023674 A1 *    2/2015    ........... G06F 3/0484

(Continued)

OTHER PUBLICATIONS

Notice of Allowance received for U.S. Appl. No. 16/046,579, dated May 7, 2021, 12 pages.

(Continued)

*Primary Examiner* — Reginald R Reyes
(74) *Attorney, Agent, or Firm* — KRAGULJAC LAW GROUP, LLC

(57) ABSTRACT

Methods and systems for managing patient attributions are provided. Interaction events between clinicians and the patient are identified, and using times associated with each interaction, a time series of the interactions for each clinician may be constructed. Care responsibility curves measuring a clinician's care responsibility level over time may be generated using the time series, an initial care responsibility level assigned to each interaction and a rate of decay for each interaction, which may be based on the type of action and type of clinician who interacted with the patient. A care responsibility score for each clinician may be determined from the clinician's care responsibility curve, and a patient-attribution assignment record may be created to attribute the patient to one of the clinicians based on a ranking of the clinicians' care responsibility scores.

20 Claims, 11 Drawing Sheets

(56) References Cited

U.S. PATENT DOCUMENTS

| | | | |
|---|---|---|---|
| 2012/0253886 A1* | 10/2012 | Nelson | G06Q 10/06 705/7.31 |
| 2014/0122100 A1* | 5/2014 | Fillmore | G16H 40/20 705/2 |
| 2015/0012298 A1* | 1/2015 | Ash | G16H 15/00 705/3 |
| 2016/0092641 A1* | 3/2016 | Delaney | G16H 40/20 705/3 |
| 2017/0185723 A1* | 6/2017 | McCallum | G06Q 10/10 |
| 2018/0150604 A1* | 5/2018 | Arena | G06Q 10/06393 |
| 2019/0035502 A1 | 1/2019 | Roberts et al. | |

FOREIGN PATENT DOCUMENTS

| | | |
|---|---|---|
| WO | 2018/044807 A1 | 3/2018 |
| WO | 2018044807 A1 | 3/2018 |

OTHER PUBLICATIONS

Non-Final Office Action received for U.S. Appl. No. 16/046,579, dated Apr. 9, 2020, 17 pages.
U.S. Patent and Trademark Office (USPTO), Notice of Allowance issued in U.S. Appl. No. 16/046,579 dated May 5, 2021 (12 pgs).
U.S. Patent and Trademark Office (USPTO), Notice of Allowance issued in U.S. Appl. No. 16/046,579 dated Sep. 9, 2021 (6 pgs).
U.S. Patent and Trademark Office (USPTO), Notice of Allowance and AFCP 2.0 Decision issued in U.S. Appl. No. 16/418,270 dated Jun. 5, 2023 (9 pgs).

* cited by examiner

SYSTEMS AND METHODS FOR MANAGING CAREGIVER RESPONSIBILITY

CROSS-REFERENCE TO RELATED APPLICATIONS

This application claims the benefit of U.S. Provisional Application No. 62/611,646 titled "SYSTEMS AND METHODS FOR MANAGING CAREGIVER RESPONSIBILITY," filed on Dec. 29, 2017, which is hereby expressly incorporated by reference in its entirety.

BACKGROUND

Accountable Care Organizations (ACOs) use various measures aimed to lower health care costs and provide high quality of care to patient populations, including holding care providers responsible for the care provided to patients. To do this, patients within a population are attributed to certain care providers who are held responsible for the patient's cost and quality of care regardless of whether other care providers also interacted with the patient. Conventional methods for patient attribution, however, either do not provide for real-time tracking and do not always accurately reflect who should be held responsible for a patient because such methods are based on the quantity of interactions or services without considering the context. Accordingly, care providers are not often able to efficiently manage the patients attributed to them during a given time period. Additionally, when patient attribution does not consider the context of interactions between clinicians and patients, clinicians who should be held responsible for a patient may be missed while those providers who are held responsible may have had less to do with the outcome and costs, thereby frustrating the goal of using incentives to lower costs and provide good quality of care.

SUMMARY

Systems, methods and computer-readable media are provided for creating or determining a patient-attribution assignment that attributes a particular patient to a particular clinician in a way that accurately reflects who should be held responsible for the patient's care and, in some aspects, using the patient-attribution assignments for notifying an appropriate clinician of the patient's condition or for performing other actions. In particular, a patient-attribution system is provided for generating patient-attribution assignments based on clinicians' interactions with a patient and/or the patient's care process, including ranking clinicians based on the relative degree that each clinician contributed to the patient's care.

Embodiments automatically track clinicians' interactions with the patient and attribute a care responsibility level for each interaction. The care responsibility level for an action may decay over time, and a particular rate of decay may be determined by the type of interaction and the type of clinician who interacted with the patient. Care responsibility curves generated using the times the interactions occurred and the rates of decay may be used to determine care responsibility scores for each clinician. The clinicians may be ranked using the care responsibility scores, and a patient-attribution assignment is created to attribute a particular patient with a particular clinician based on the ranking. One aim of the disclosure is to provide an accurate and up-to-date representation of a patient attribution and, in some aspects, notify the responsible clinician of events relating to the patient's condition. Additionally, the patient-attribution assignments may be used in conjunction with information regarding the patient's outcome and care costs to evaluate the clinician.

BRIEF DESCRIPTION OF THE DRAWINGS

The present invention is described in detail below with reference to the attached drawing figures, wherein.

DETAILED DESCRIPTION

Figure 1A:
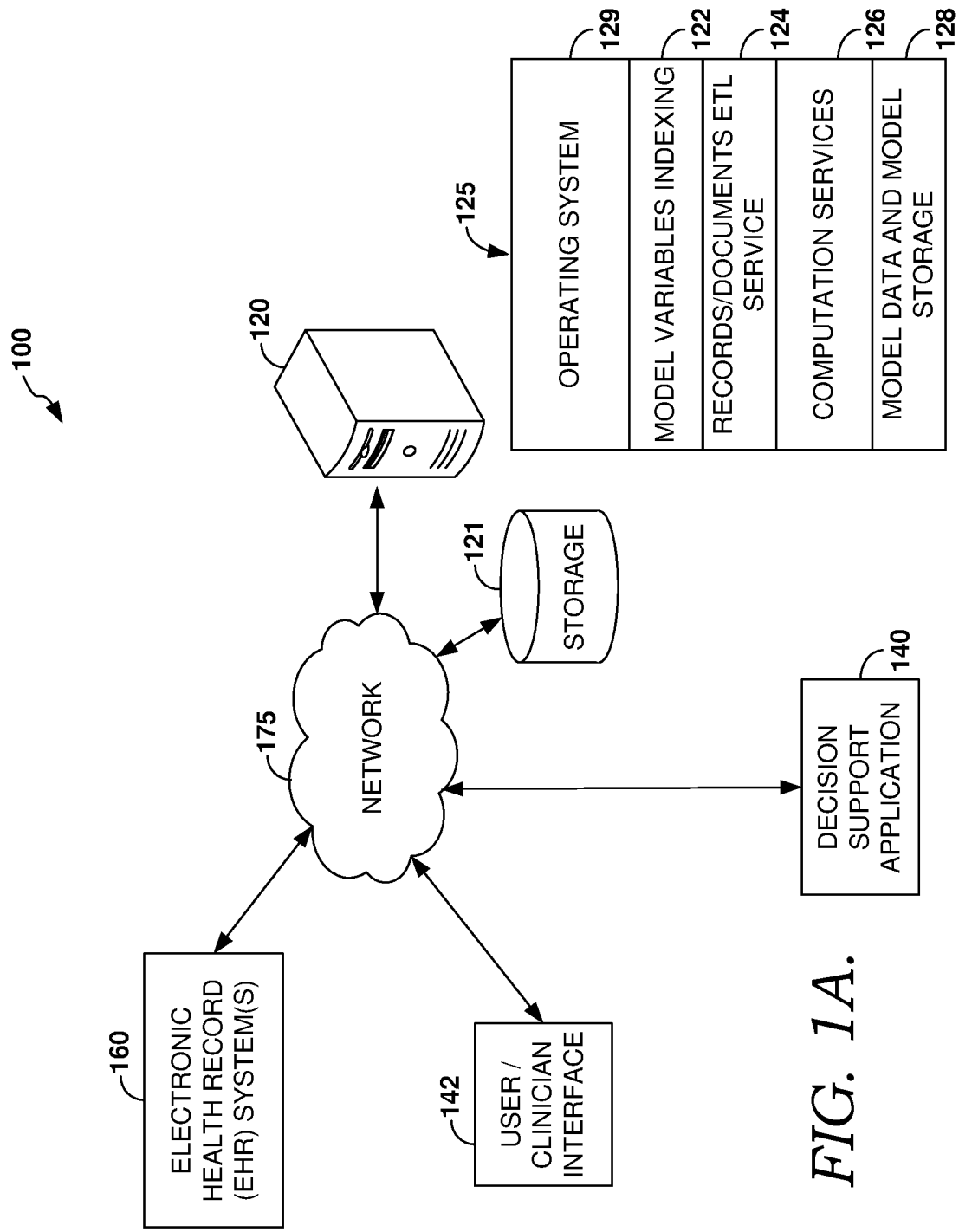
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media, as discussed further with respect to FIGS. 1A-1B.

Accordingly, at a high level, this disclosure describes, among other things, methods and systems for managing patient attribution, or the assignment of a patient to a responsible caregiver, such as a clinician. In some embodiments, the methods and systems may be implemented as a decision support computer application or tool and may be part of a more comprehensive healthcare decision support application for monitoring patients and providing decision support to caregivers. Such decision support technology plays an important part of modern care processes for a patient. Embodiments described herein attribute patients to a clinician based on electronic tracking of interactions between a population of patients and clinicians, which provides an accurate representation of the particular clinician who contributed to a particular patient's care in such a way that would place responsibility on the clinician. Some embodiments of the decision support tool further use the patient-attribution assignments to determine the appropriate clinicians responsible for the patient's care and notify the those clinicians of a clinical event. Other embodiments are further used to apply cost and/or quality incentives to clinicians based on responsibility as determined by the patient-attribution assignments. In this way, the patient-attribution assignments may be used to provide a quality control evaluation for clinicians based on the outcomes of patients attributed to the particular clinician.

In particular, embodiments include interaction events between a clinician and a patient relating to the patient's care. An interaction, for example, may include an office visit, an examination, a consultation, a procedure, and the like. Interaction events are electronic events indicating that an interaction between a particular clinician and particular patient has occurred. Each interaction event identifies a time that the interaction occurs, the patient involved, and at least one clinician involved in the interaction. Clinicians may include, for example, physicians, physician assistants, nurse practitioners, registered nurses, behavior specialists, respiratory therapists, physical therapists, radiologists, pharmacists, and the like.

Over a period of time, multiple interaction events, either with the same clinician or a different clinician, for the patient may be identified, and each clinician identified with an interaction has the potential to be assigned responsibility for the patient. A time series of interactions with each clinician over the period of time may be constructed. An initial care responsibility level may be assigned to each interaction, and a care responsibility curve measuring a clinician's care responsibility level over time may be generated using the initial care responsibility level and a rate of decay for each interaction. The rate of decay is the rate at which the care responsibility level associated with the interaction decreases over time, and the rate may be based on the type of interaction and the type of the clinician who interacted with the patient. A care responsibility score for a clinician may be determined from the care responsibility curve and the time series. In some aspects, the care responsibility score is determined from the area under the care responsibility curve over the period of time. Care responsibility curves and scores may be generated for all patients within a population, with each patient being assigned to a responsible clinician based on the care responsibility scores. The assignments may be used to notify a responsible clinician of an event or may be used as an evaluation tool. Specifically, the patient-attribution assignments may be used to incentive clinicians to whom patients with good outcomes and/or low costs are attributed.

Accordingly, one aim of embodiments of this disclosure relates to deriving appropriate patient attributions that accurately reflect to whom a clinician is responsible based on previous interactions between the clinician and patient. Patient attributions are often used by Accountable Care Organizations (ACOs) that are responsible for delivering efficient and effective health care to a defined population. Through measures intended to ensure a high quality of care and lower costs, participating caregivers, such as a clinician, are held responsible for the costs and quality of care for particular patients. There are existing methods for identifying clinicians responsible for patients in the population, but these conventional systems do not accurately reflect a clinician's involvement with the patients or track responsibility in real time. At least some existing methods attribute a patient's care to a particular clinician based solely on the number of visits, which fails to consider the context of the patient visit or a clinician's actual role in the patient's care. Further, these methods are often done either prospectively or retrospectively. In the prospective model, clinicians are attributed to patients at the start of the relationship and/or the start of a particular time period; however, the patient's care plan and clinician's participation in providing for the patient's care may change during that period. Under retrospective models, attribution occurs at the end of a time period and is based on all services rendered to the patient.

There are several limitations arising from these conventional systems. For instance, under the traditional methods, there is no distinction between services provided by clinicians of different specialties. Time that has elapsed between serial encounters between a clinician and patient is not taken into consideration. Additionally, with retrospective attribution, clinicians are not aware of which patients are attributed to them until the end of the relevant time period, at which time, it may be too late to change the patient's outcome or affect achievement of pay-for-performance targets.

Accordingly, embodiments of the disclosure improve upon conventional industry practice by measuring the responsibility level of each potentially responsible clinician in a quantifiable and objective way to provide a more accurate representation of the responsible clinicians for more effective and efficient treatment and care. Embodiments receive electronic indications of interactions between a patient and clinicians and, based on the types of interaction and the types of clinicians involved, identify a clinician who is most responsible for the patient. Specifically, when an interaction, such as an office visit or procedure, is logged, a care responsibility level for a clinician associated with the interaction is set and then decreases based on the type of action and the type of the clinician. A care responsibility score may be the resulting care responsibility curve itself or may be derived from one or more care responsibility curves. The care responsibility score may be used to rank the clinician's involvement relative to other potentially responsible clinicians. One or more responsible clinicians will be determined based on the care responsibility scores.

The care contribution score may be used for notifying appropriate clinician(s) of a clinical event related to the patient. In some embodiments, a clinical event may include a diagnosis, procedure, testing, or patient inquiry. For instance, when a patient is in need of emergency care, the responsible clinician may be automatically notified to either provide the care or to provide information that may be relevant to another clinician providing care. In another example, a patient or patient's representative may have an inquiry regarding the patient's care and/or health, and the patient-attribution assignments may be used to identify the responsible clinician. Similarly, when another clinician, such as a nurse, notices an issue with the patient's care or condition, that clinician may determine who to notify based on the patient-attribution assignment.

Patient-attribution assignments may be made for a plurality of patients, and all the patients attributed to or assigned to a particular clinician may be aggregated into a population. The assigned population may then be used to evaluate the care provided by the particular clinician. In this way, embodiments of the disclosure track who will be attributed to the clinician during the current period so the clinician can manage the patients proactively. Further, in some embodiments, the assignments are used to evaluate the clinician's care of the population. For example, the attribution assignments are used to determine the patient outcomes for which a clinician is held responsible and use the patient outcomes to evaluate the clinician's care. Similarly, assignments may be used to determine the cost of care for patients attributed to a clinician, which is often used by ACOs. Further, in some aspects, a risk index for the patients to which a clinician is held responsible is used to determine a panel weight for evaluating clinicians based on patient outcomes or cost of care. In this way, outcomes and/or costs of care may be normalized across clinicians with patients of varying risk levels for evaluating the clinician.

Additionally, updates to the patient's care based on new interactions may be automatically acquired by embodiments of the present disclosure to assess the level of responsibility of one or more clinicians in real time, which provides for an accurate representation of responsibility in real time and, ultimately, more efficient care when needed. Further, in some aspects, the interactions that trigger a care level assignment may already be interactions documented in the patient's electronic health record or claims data, or otherwise electronically tracked such that no additional steps outside of the usual care protocol need to be taken by clinicians or staff. Accordingly, patient attribution may be done in real-time (rather than prospectively or retroactively), which helps a clinician determine how to manage the care of patients with whom the clinician interacts, resulting in more effective and efficient care. Although the information may be already documented, this information represents new sources of information for identifying responsible clinicians and creating care responsibility curves. Utilizing these non-conventional sources of information to create care responsibility curves is a non-conventional technique in making patient-attribution assignments that allows for a more accurate and updated representation of the appropriate attributions for a given clinician or population of patients.

Referring now to the drawings in general and, more specifically, referring to FIG. 1A, an aspect of an operating environment 100 is provided suitable for practicing an embodiment of this disclosure. Certain items in block-diagram form are shown more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure aspects of the invention. Thus, for readability, items are shown and referenced in the singular (while fully contemplating, where applicable, the plural). Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer-readable media having machine-readable application software embodied thereon. In this regard, a machine-readable storage media may be any tangible medium that can contain, or store a software application for use by the computing apparatus.

As shown in FIG. 1A, example operating environment 100 provides an aspect of a computerized system for compiling and/or running an embodiment of a computer-decision support tool for creating patient-attribution assignments based on clinician interactions with patients. Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, the functions performed by these components, or the services carried out by these components may be implemented at appropriate abstraction layer(s), such as the operating system layer, application layer, hardware layer, etc., of the computing system(s). Alternatively, or in addition, the functionality of these components and/or the embodiments described herein can be performed, at least in part, by one or more hardware logic components. For example and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example operating environment 100, it is contemplated that, in some embodiments, functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems, and may be implemented in computer system 120. Similarly, EHR system 160 may perform functions for two or more of the EHR systems (not shown). In an embodiment, EHR system 160 includes historical claims data for health services, apportionment data, and related health services financial data.

In some embodiments of the technologies described herein, sequence itemset mining is performed using data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system. It comprises a large 'transaction database' in which each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, the acute or chronic nature of the health conditions that pertain to the patient, the rate of change of the severity of the health conditions, or other factors. Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks, such as a cellular network or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health-related records, which may be stored on storage 121, and may further include one or more computers or servers that facilitate the storing and retrieval of the health records. In some embodiments, EHR system 160 and/or other records systems may be implemented as a cloud-based platform or may be distributed across multiple physical locations. EHR system 160 may further include record systems, which store real-time or near real-time patient (or user) information, such as wearable sensor or monitor, bedside, or in-home patient monitors or sensors, for example. Although FIG. 1A depicts an example EHR system 160, it is contemplated that an embodiment relies on decision support application 140 for storing and retrieving patient record information.

Example operating environment 100 further includes a user/clinician interface 142 and decision support application 140, each communicatively coupled through network 175 to an EHR system 160. Although environment 100 depicts an indirect communicative coupling between interface 142 and application 140 with EHR system 160 through network 175, it is contemplated that an embodiment of interface 142 or application 140 are communicatively coupled to EHR system 160 directly. An embodiment of decision support application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet and may be used to provide or manage user services provided by an embodiment of the technologies described herein, which may be used by a caregiver to provide, for example, information relating to patient attribution, including suggestions for a patient-attribution assignment. In some embodiments, application 140 includes or is incorporated into a computerized decision support tool, as described herein. Further, some embodiments of application 140 utilize user/clinician interface 142.

In some embodiments, application 140 and/or interface 142 facilitate accessing and receiving information from a user or healthcare provider about a specific patient or set of patients, according to the embodiments presented herein. Embodiments of application 140 also may facilitate accessing and receiving information from a user or healthcare provider and facilitates the display of results, recommendations, or orders, for example. The information accessed, received, and/or displayed includes information about a specific patient, caregiver, or population including historical data; healthcare resource data; variables measurements, time series, and patient-attribution assignments described herein; or other health-related information. In an embodiment, application 140 also facilitates receiving orders, staffing scheduling, or queries from a user based on the results of monitoring patient interactions for determining responsibility levels for each clinician, which may, in some embodiments, utilize user interface 142. Decision-Support application 140 may also be used for evaluation of the performance of various embodiments.

In some embodiments, user/clinician interface 142 may be used with application 140, such as described above. One embodiment of user/clinician interface 142 comprises a user interface that may be used to facilitate access by a user (including a healthcare provider or patient) to an assigned clinician, patient, or patient population. One embodiment of interface 142 takes the form of a graphical user interface and application, which may be embodied as a software application (e.g., decision support application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application, which may take the form of an applet or app, or a set of applications usable to manage user services provided by an embodiment of the technologies described herein.

In some embodiments, interface 142 may facilitate providing the output of the determined patient-attribution assignments, recommendations for patient-attribution assignments (including recommended responsible clinicians by role or individual based on previous outcomes), care responsibility curves for an individual patient or population of patients; providing instructions or outputs of other actions described herein; and logging and/or receiving other feedback from the user/caregiver, in some embodiments. Interface 142 also may be used for providing diagnostic services or evaluation of the performance of various embodiments.

Example operating environment 100 further includes computer system 120 that may take the form of one or more servers and that is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations, such as one or more local clients and one or more remote servers, and may be distributed across the other components of example operating environment 100. For example, aspects of decision support application 140 or user/clinician interface 142 may operate on or utilize computer system 120. Similarly, a portion of computing system 120 may be embodied on user/clinician interface 142, application 140, and/or EHR system 160. In one embodiment, computer system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which, in some embodiments, operates in the cloud, as a distributed system on a virtualization layer within computer system 120, and includes operating system 129. Operating system 129 may be implemented as a platform in the cloud and is capable of hosting a number of services such as 122, 124, 126, and 128. Some embodiments of operating system 129 comprise a distributed adaptive agent operating system. Embodiments of services 122, 124, 126, and 128 may run as local services or may be distributed across one or more components of operating environment 100, in the cloud, on one or more personal computers or servers such as computer system 120, and/or a computing device running interface 142 or application 140. In some embodiments, interface 142 and/or application 140 operate in conjunction with software stack 125.

In embodiments, model variables indexing service 122 and records/documents ETL service 124 provide services that facilitate retrieving actions performed for a patient that are electronically recorded in the patient's EHR. Services 122 and/or 124 may also provide services for retrieving and extracting patient physiological variables and interaction events, which may include frequent itemsets; extracting database records; and cleaning the values of variables in records. For example, services 122 and/or 124 may perform functions for synonymic discovery, indexing or mapping variables in records, or mapping disparate health systems' ontologies. In some embodiments, these services may invoke computation services 126.

Computation services 126 may perform statistical or computing operations such as computing functions or routines for determining decay rates or curves, as further described herein. Computation services 126 also may include natural language processing services (not shown) such as Discern nCode™ developed by Cerner Corporation, or similar services. In an embodiment, computation services 126 include the services or routines that may be embodied as one or more software agents or computer software routines. Computation services 126 also may include services or routines for utilizing one or more models, including logistic models, for determining the care responsibility scores and the appropriate patient-attribution assignments, such as the models described in connection to FIGS. 2-7. In some embodiments, computation services 126 use EHR system(s) 160, model data and model storage services 128, and/or other components of example operating environment 100, and may also include services to facilitate receiving and/or pre-processing data. Model data and model storage services 128 may be utilized to perform services for facilitating storage, retrieval, and implementation of the models described herein and of the data used in the models.

Some embodiments of stack 125 may further comprise services for utilizing an Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing services may be embodied using IBM InfoSphere stream processing platform, Twitter Storm stream processing, Ptolemy or Kepler stream processing software, or similar complex event processing (CEP) platforms, frameworks, or services, which may include the use of multiple such stream processing services in parallel, serially, or operating independently. Some embodiments of the invention also may be used in conjunction with Cerner Millennium®, Cerner CareAware® (including CareAware iBus®), Cerner CareCompass®, or similar products and services.

Example operating environment 100 also includes storage 121 (also referred to herein as data store 121), which in some embodiments includes patient data for a patient (or information for multiple patients), including raw and processed patient data; variables associated with patient recommendations; and information pertaining to clinicians and staff, including healthcare provider policies and shift schedules. Data store 121 may further include recommendation knowledge base; recommendation rules; recommendations; recommendation update statistics; an operational data store, which stores events, frequent itemsets (such as "X often happens with Y", for example), and itemsets index information; association rulebases; agent libraries, solvers and solver libraries, and other similar information, including data and computer-usable instructions; patient-derived data; and healthcare provider information, for example. It is contemplated that the term "data" includes any information that can be stored in a computer storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
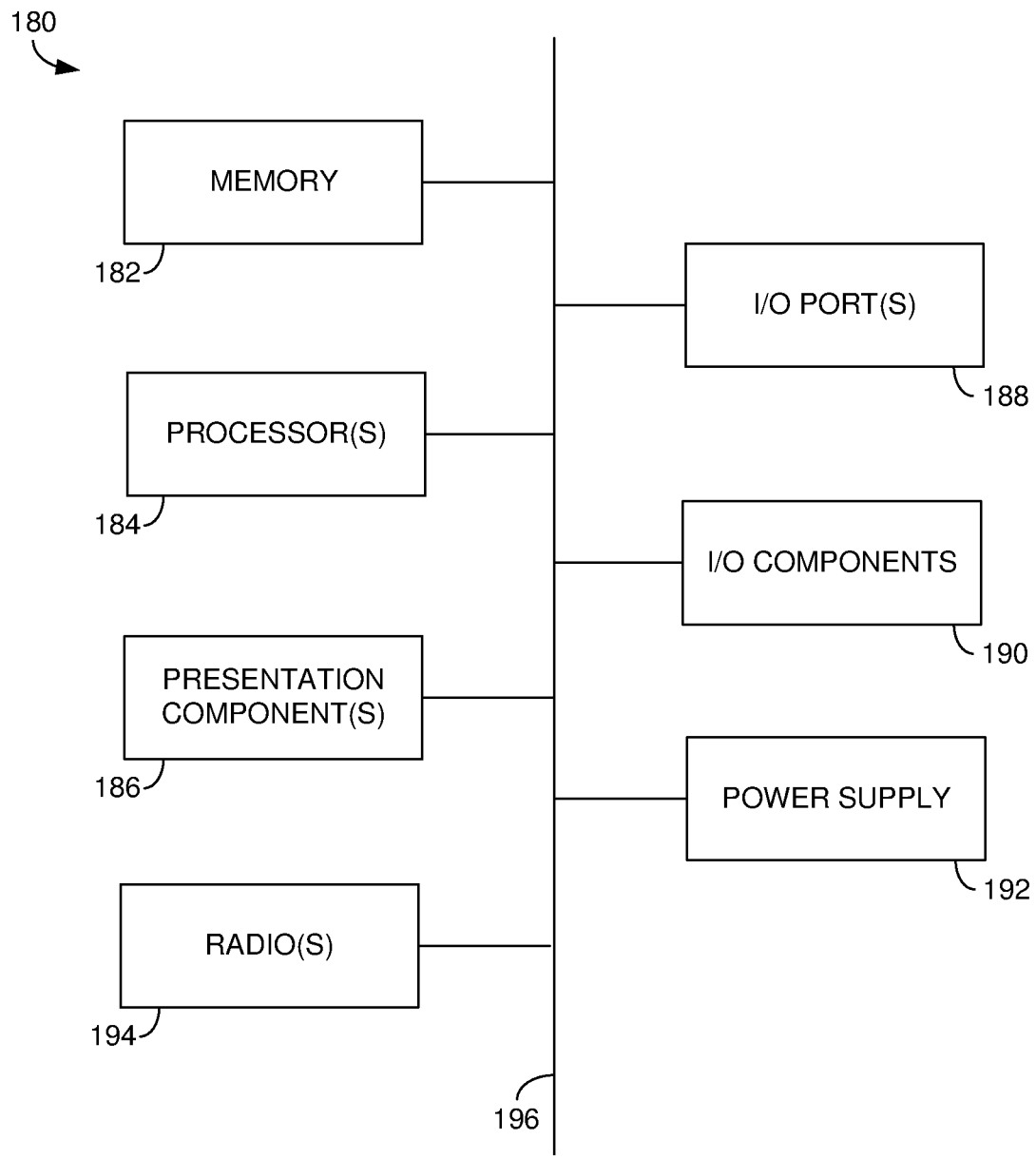

Turning briefly to FIG. 1B, there is shown one example embodiment of computing system 180 representative of a system architecture that is suitable for computer systems such as computer system 120. Computing device 180 includes a bus 196 that directly or indirectly couples the following devices: memory 182, one or more processors 184, one or more presentation components 186, input/output (I/O) ports 188, input/output components 190, radio 194, and an illustrative power supply 192. Bus 196 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an exemplary computing system that can be used in connection with one or more embodiments of the present invention. Distinction is not made between such categories as "workstation," "server," "laptop," "hand-held device," etc., as all are contemplated within the scope of FIG. 1B and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 180. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 182 includes computer storage media in the form of volatile and/or nonvolatile memory. The memory may be removable, non-removable, or a combination thereof. Exemplary hardware devices include solid-state memory, hard drives, optical-disc drives, etc. Computing system 180 includes one or more processors that read data from various entities such as memory 182 or I/O components 190. Presentation component(s) 186 present data indications to a user or other device. Exemplary presentation components include a display device, speaker, printing component, vibrating component, etc.

In some embodiments, computing system 194 comprises radio(s) 194 that facilitates communication with a wireless-telecommunications network. Illustrative wireless telecommunications technologies include CDMA, GPRS, TDMA, GSM, and the like. Radio 194 may additionally or alternatively facilitate other types of wireless communications including Wi-Fi, WiMAX, LTE, or other VoIP communications. As can be appreciated, in various embodiments, radio 194 can be configured to support multiple technologies and/or multiple radios can be utilized to support multiple technologies.

I/O ports 188 allow computing system 180 to be logically coupled to other devices, including I/O components 190, some of which may be built in. Illustrative components include a microphone, joystick, game pad, satellite dish, scanner, printer, wireless device, etc. The I/O components 190 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 180. The computing system 180 may be equipped with depth cameras, such as stereoscopic camera systems, infrared camera systems, RGB camera systems, touchscreen technology, and combinations of these, for gesture detection and recognition. Additionally, the computing system 180 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
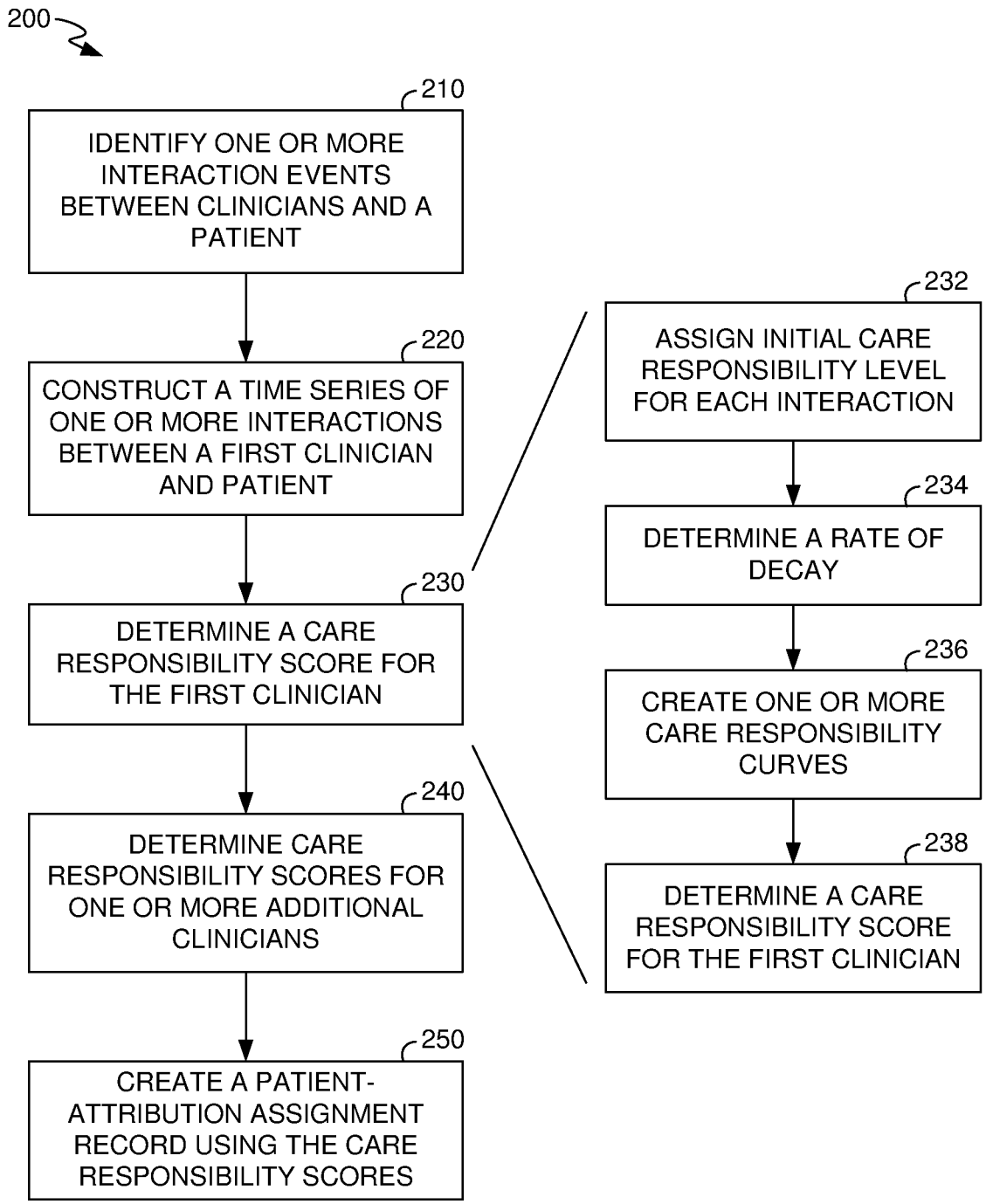
FIG. 2 depicts a flow diagram of a method for providing a decision support system for attributing a patient to a particular clinician, in accordance with an embodiment of the disclosure.

Turning now to FIG. 2, one example embodiment of a method for creating a patient-attribution assignment is provided and is referred to generally as method 200. In particular, example method 200 utilizes the time series of interactions between a clinician and a patient to determine a care responsibility score for each clinician/patient combination and creates a patient-attribution assignment based on the care responsibility scores of each clinician interacting with the patient. This method provides an accurate representation of the patients for whom a clinician should be assigned responsibility based on patient-clinician interactions by attributing patients to clinicians who contribute more to the patient's care while taking into account the context of the interactions. In some embodiments, method 200 is suitable for implementation as a computer-performed decision support tool or application for making patient-attribution assignments and, thus, providing patient-attribution assignments that are more updated and accurately reflect the responsible clinicians compared to conventional technology.

In accordance with method 200, at step 210, a plurality of interaction events indicating interactions between clinicians and patients is identified. Each interaction is a clinician's interaction with a patient's care process. An interaction, for example, may include an office visit, an examination, a consultation, a procedure (including inpatient and outpatient surgeries), a referral, and the like. In some aspects, inpatient procedures and outpatient procedures are considered different interaction types. These example interactions are not intended to be limiting as it is contemplated that other interactions with the patient, either directly or indirectly through the patient's care process, may be performed and received in accordance with aspects of this invention.

The interaction events that are identified may be for a population of patients, such as a population of patients receiving care within the same health care provider system, with the same insurance carrier, within a defined geographical region, or who are associated with a particular health care facility. During the span of a period of time, there may be several interactions for each patient that involve different clinicians, and each interaction may trigger an interaction event that is identified in accordance step 210. Accordingly, the plurality of interaction events may provide indicators of interactions for different patient-clinician combinations. Each patient-clinician combination (also referred to herein as a patient-clinician pair) is a combination of a particular patient and a particular clinician who interacted with each other (either directly or indirectly). Each interaction event may identify a time that the interaction occurred, a type of interaction, the patient involved, and at least one clinician involved in the interaction.

The interaction events may be identified through receipt of data from a data storage component or may be identified from data received directly from a device, such as a sensor, being used during the interaction. In exemplary embodiments, for instance, the interaction events are identified from the patient's EHR, such as a medical EHR within EHR system 160 in FIG. 1, or from claims data storage. Data indicating an interaction may be received from the patient's EHR or another data source used by the healthcare provider in the normal course of the patient's care, such as the coding data for a patient's visit. In other words, clinicians do not need to perform additional steps for recording these interactions for use with embodiments of this disclosure but, rather, embodiments of the disclosure leverage information that is already available to track the patient-clinician interactions. Additionally, embodiments of step 210 may acquire data indicating interaction events continuously, periodically, or at non-regular intervals. In exemplary embodiments, the interaction events are identified in real time or substantially real time.

At step 220, a time series of the interactions is constructed for a first clinician and a patient. The time series indicates when interactions between the first clinician and the patient occur over a period of time. In some instances, the period of time may be a pre-determined span of time, such as a period of one week, one month, one year, or two years. In other instances, the period of time may be specific to the patient, such as the length of a patient's hospital admission, illness, or lifetime.

At step 230, a care responsibility score is determined for the first clinician. The care responsibility score is a measure of a clinician's responsibility for a particular patient for a given period of time. The care responsibility score may be determined from the time series of interactions and care responsibility curves created from the time series. Accordingly, to determine the care responsibility score for the first clinician, an initial care responsibility level for each interaction is assigned, as shown in step 232 of FIG. 2. The care responsibility level is an indication of the level of responsibility a clinician is considered to have for a patient and reflects the amount of involvement and responsibility clinician has. The curves indicate a change in the care responsibility level as a function of time; for instance, during a given time interval, a care responsibility level indicated by the curve may be less than or equal to a maximum level of responsibility and greater than or equal to no responsibility. (See e.g., curve 420 of FIG. 5.) For example, in some aspects, a clinician's care responsibility level is between 1 and 0, with 1 being the highest amount of care responsibility and 0 being the lowest amount of care responsibility. In exemplary embodiments, the initial care responsibility level is pre-determined and, in some instances, is the same for each type of action. For instance, each time a clinician interacts with a patient, the care responsibility level for the clinician may be set at the maximum care responsibility level, such as 1. It is contemplated that, in other aspects, the initial care responsibility level depends on the type of interaction being taken. For example, interactions that require more time or attention from a clinician or that are generally considered to carry a greater responsibility may provide a higher initial care responsibility level, such as performing an inpatient procedure, compared to interactions requiring less time or carry less responsibility, such as a patient visit.

The care responsibility levels may change or decay over time, reflecting the natural decrease in the interaction's relevance as the interaction becomes further removed in time. Accordingly, at step 234 of method 200, a rate of decay of the care responsibility level for each interaction between the first clinician and the patient is determined. An interaction may trigger a clinician's care responsibility level to be set at 1, for example, and the clinician's care responsibility level may decrease to 0 if there are no subsequent interactions associated with the clinician for that patient prior to reaching a care responsibility level of 0.

In exemplary aspects, the rate of decay depends both on the clinician type and interaction type. A clinician type may relate to a clinician specialty and may include, for instance, a cardiologist, surgeon, primary care physician, pediatrician, neurologist, oncologist, and the like. An interaction type may indicate the context of the interaction between the clinician and the patient and may include, for instance, an office visit (also referred to herein as a patient visit), a follow-up visit, a referral, a consultation, an examination, a procedure (such as outpatient procedure or patient procedure), and the like. These examples for clinician type and interaction type are illustrative and not intended to be limiting.

As it may be appreciated, the amount of responsibility accompanying different types of clinicians and types of interactions may vary. Accordingly, different combinations of clinician-interaction types may be grouped into tiers having different resulting rates of decays. The tiers may be based on a determination of which clinician type/interaction type combinations should have the longest-lasting effect on a care responsibility level based on the amount of responsibility and involvement typically associated with the types of clinicians and interactions. Clinician and interaction types that are afforded greater responsibility have slower rates of decays than other clinician-interaction types. In some embodiments, the tier is further based on a correspondence between the patient's diagnosis and the interaction type and/or clinician type. Where there is a correspondence between a diagnosis and the interaction type and/or clinician type, more responsibility may be attributed. For instance, a cardiologist who sees a patient for a visit relating to a heart condition diagnosis may be afforded more responsibility than a cardiologist who sees a patient for a general wellness visit.

The different rates of decay for each tier may be effected through different alpha ($\alpha$) and beta ($\beta$) values as shown in Table 1 below.

TABLE 1

Example Parameters for Care Responsibility Curves

| Tier ($\Gamma$) | Alpha ($\alpha$) | Beta ($\beta$) |
|---|---|---|
| 1 | 1.33 | 3.0 |
| 2 | 2.0 | 4.0 |
| 3 | 4.0 | 5.0 |
| 4 | 10.0 | 6.0 |
| 5 | 30.0 | 8.0 |

In exemplary embodiments, the rate of decay is determined using a phase transition to produce a curve, which is also referred to herein as a care responsibility curve. For example, the phase transition function used may be: where $\Lambda_j^k(t)$ is the most recent time ($\leq t$) when patient, $P_j$, is seen by clinician, $D_k$. Additionally, $\Gamma_j^k$ refers to the tier of the most recent encounter when patient $P_j$ is seen by clinician, $D_k$. In this way, $\{P_j\}_{j=1}^N$ denotes a population of patients, and $\{D_k\}_{K=1}^N$ denotes a group of clinicians.

Using the rates of decay and the initial care responsibility levels, at step 236, one or more care responsibility curves are generated. Care responsibility curves illustrate the change(s) in a clinician's care responsibility level for a particular patient over a period of time, with the changes being determined from the rate(s) of decay.

Figure 3:
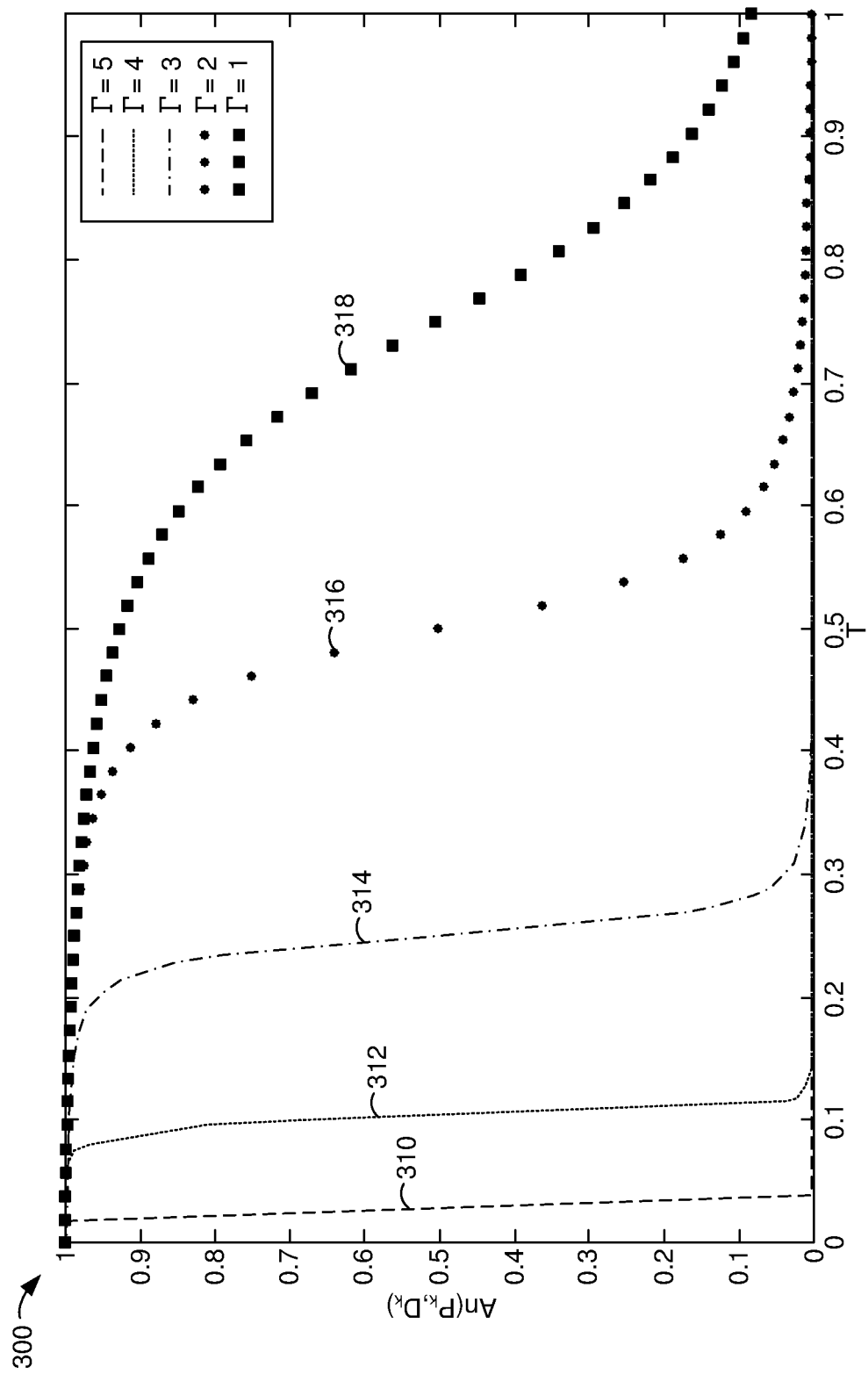
FIG. 3 depicts care responsibility curves for each tier based on a type of interaction and a type of clinician, in accordance with an embodiment of the disclosure.

FIG. 3 depicts a graphical representation 300 of example care responsibility curves 310, 312, 314, 316, and 318 that each corresponds to a tier in Table 1. Each curve is based on an action occurring at t=0, and t is measured in portions of a time period. The care responsibility levels for the curves begin to decay at different times and, once decay begins, decay at different rates. The tier 5 curve 310 begins to decay relatively soon after the interaction occurs and decays at the quickest rate with the care responsibility level being fully decayed within approximately 0.04 units of t. The tier 1 curve 318 does not decay until approximately 0.3 units of t after the interaction and is not even fully decayed at time t=1.

Figure 4:
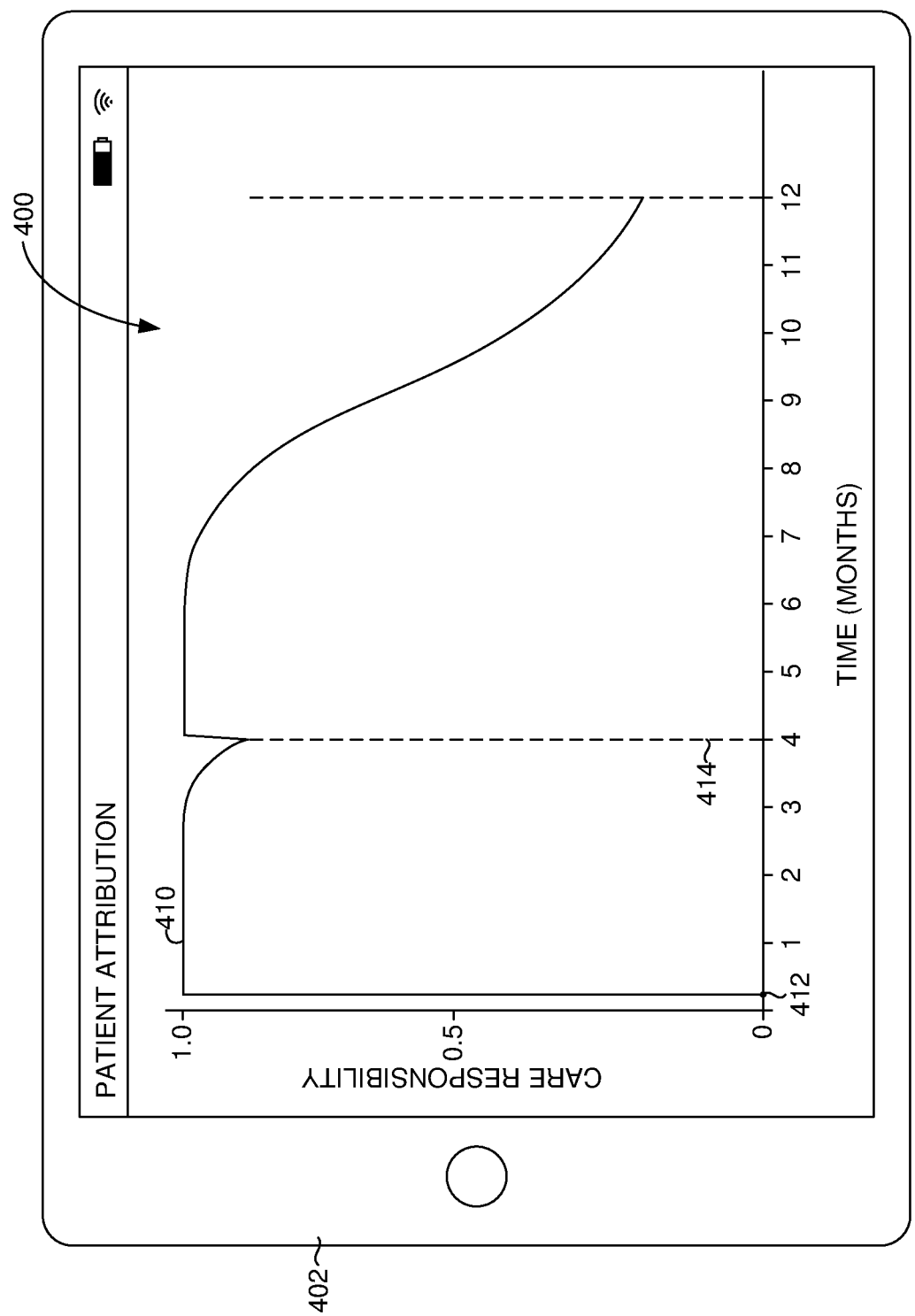
FIG. 4 depicts an example user interface with a care responsibility curve generated for a clinician based on two patient interactions, in accordance with an embodiment of the disclosure.

In some embodiments, a graphic user interface, such as interface 142 of FIG. 1A, may be generated with one or more care contribution curves for one or more particular clinician-patient pair. FIG. 4, for instance, depicts a graphic user interface 400 for presentation on user device 402. Graphic user interface 400 is generated to include care responsibility curve 410 for a clinician interacting with a particular patient. In this example, curve 410 may represent the care responsibility level of the patient's primary care physician who saw the patient for a patient visit within the first month of the set time period, denoted as interaction time 412. The interaction time 412 is the time associated with the interaction between the clinician and the patient. In some aspects, the interaction time 412 is the time that an interaction is electronically logged. For instance, when a clinician completes an electronic order for the patient, the interaction will be logged at that time, and the log time may be automatically associated with the interaction and used for the interaction time 412. The interaction time 412 may also be the time the interaction, or a portion thereof, is documented within the patient's EHR or submitted as insurance claims documentation. In some instances, the interaction time may also be entered or adjusted manually by a user.

This interaction at interaction time 412 causes the primary care physician's care responsibility level to be set at a pre-determined initial level, such as the maximum level of 1.0. In this example, the clinician and interaction types for the interaction at time 412 fall into tier 1, and, as such, the care responsibility level does not start to decay until approximately three months into the time period. When a clinician has multiple interactions with a patient, each interaction either maintains or resets the care responsibility level to the initial responsibility level (such as the maximum responsibility level of 1), and the curve begins to decay until it either reaches 0, the time period expires, or another action occurs. As shown in FIG. 4, prior to the care responsibility level fully decaying after interaction time 412, the patient has another patient visit with the primary care physician at interaction time 414, which is approximately four months after the start of the time period. This second interaction with the primary care physician creates a tier 1 curve that slowly starts to decay before seven months and is not fully decayed at the end of the one-year time period. As these interactions occur, curve 410 on graphic user interface 400 may also be updated such that a user may view the interface 400 to quickly ascertain an accurate and up-to-date responsibility level of the physician.

In some embodiments, when there are simultaneous or near simultaneous actions or overlapping curves from subsequent actions, the maximum curve is utilized. For instance, if there were a third interaction between the primary care physician and the patient within a de minimis time period, such as two days, after interaction time 414, and the third interaction resulted in a different rate of decay, the slowest decay rate between the two interactions is used for the curve.

Returning to method 200, once rates of decay are determined and care responsibility curves are generated, method 200 includes determining a care responsibility score for the clinician, at step 238. The care responsibility score may comprise a composite or overall care responsibility level. In some embodiments, the care responsibility score is one or more care responsibility curves themselves. In other embodiments, the care responsibility score may be determined using the times series and the care responsibility curves. In exemplary embodiments, for instance, the care responsibility score may be referred to as the normalized care responsibility and comprises the area under the care responsibility curve (AUC). In some instances, the care responsibility score is the AUC divided by the pre-determined time period, which is one year in the example in FIG. 4. When the care responsibility curve is a function of a period of time (such as when AUC is divided by the time period), method 200 may include receiving a time or time frame. For example, the method 200 may comprise receiving the current time and determining the period of time to be the time from a pre-determined start date (such as a calendar start date) or the start of the patient's treatment to the current time received. In other aspects, the time or time period received may be a previous time. For instance, a user may be interested in learning what the patient-attribution assignment was or should have been at a previous point in time. In that case, the time received may be a past time and the relevant period of time used to calculate the care responsibility score is a period of time looking back starting with the past time.

Figure 5:
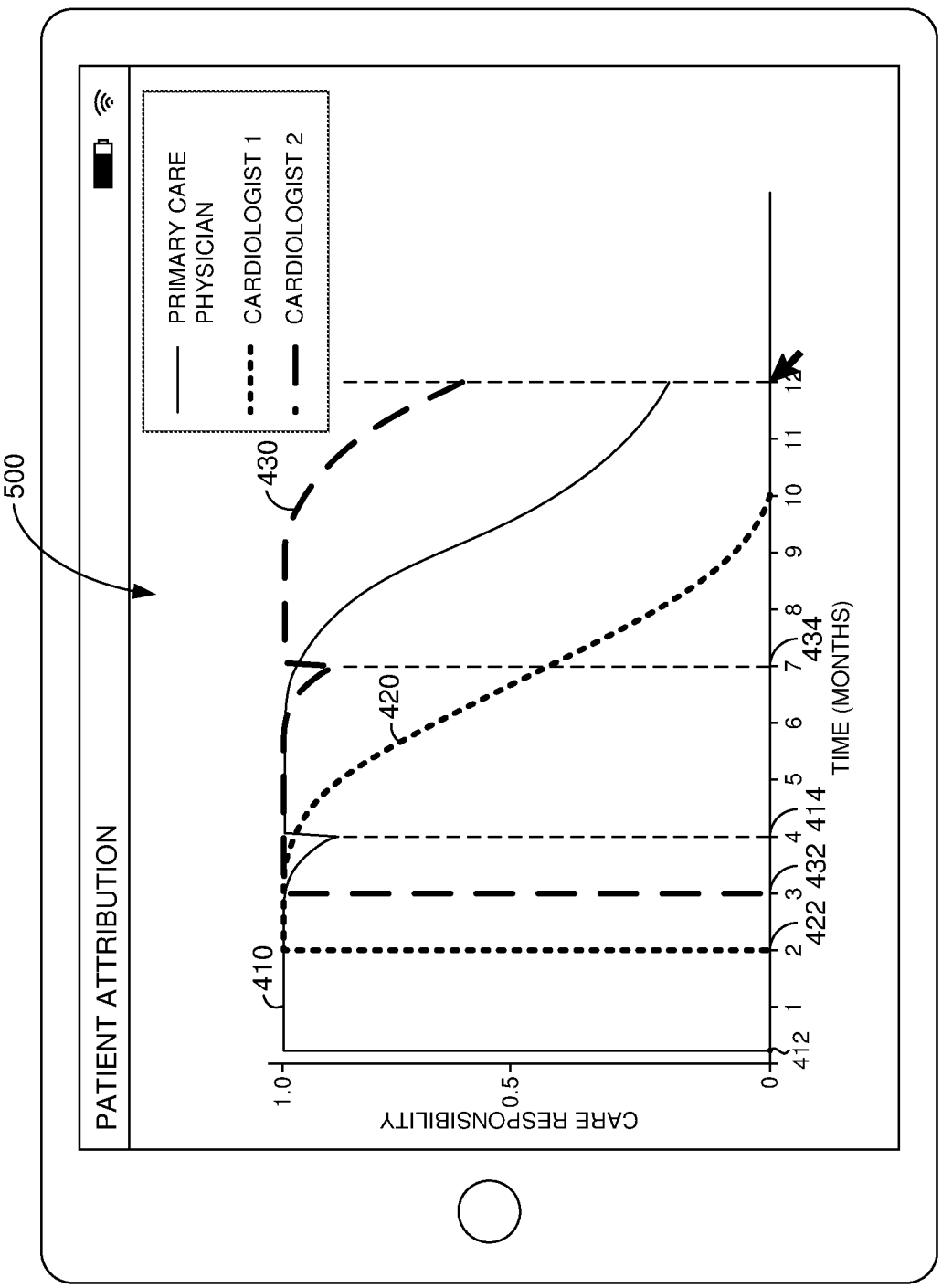
FIG. 5 depicts an example user interface with care responsibility curves generated for multiple clinicians who interact with the same patient, in accordance with an embodiment of the disclosure.

As previously discussed, patients may interact with multiple clinicians, and, as such, exemplary embodiments include determining care responsibility scores for multiple clinicians. Accordingly, at step 240, method 200 involves determining the care responsibility scores for one or more additional clinicians. These scores may be determined using care responsibility curves for these additional clinicians. FIG. 5 depicts a graphic user interface 500 generated to help a user identify relative care responsibility levels of multiple clinicians using the care responsibility curves. Graphic user interface 500 includes curve 410 of the primary care physician from the example in FIG. 4 but further includes care responsibility curves reflecting interactions between the patient and other clinicians. Specifically, curve 420 represents care responsibility levels for cardiologist 1 while curve 430 represents care responsibility levels for cardiologist 2.

In this example embodiment, curves 410, 420, and 430 indicate that the patient interacted with cardiologist 1 and cardiologist 2 between the two interactions with the primary care physician. Similar to curve 410 of the primary care physician in FIG. 4, interactions with associated time stamps are received for each cardiologist. The care responsibility level for each cardiologist is set to 1.0 at the time of their respective interactions with the patient, and the respective levels begin to decay in accordance with the appropriate tier. For instance, the patient may have seen cardiologist 1 for a patient visit at interaction time 422 (approximately 2 months from the beginning of the time period) and was then referred to cardiologist 2, who saw the patient at interaction time 432 (approximately 3 months) and again at interaction time 434 (approximately 7 months).

After the rates of decay are determined and care responsibility curves are generated, care responsibility scores for cardiologist 1 and cardiologist 2 are computed in the same manner as the score for the primary care physician described with respect to FIG. 4. Specifically, the care responsibility score may comprise the area under the care responsibility curve (AUC) and, in some instances, is divided by the pre-determined time period, which is one year in the example in FIG. 5.

At step 250, a patient-attribution assignment record may be created based on the care responsibility scores for the clinicians. The patient-attribution assignment record may comprise an electronic record of an assignment of a particular patient to a particular clinician. The patient-attribution assignment record may be stored in a database. In exemplary aspects, the assignment record may be created upon comparing care responsibility scores for multiple clinicians interacting with the patient. Accordingly, in the example embodiment of FIG. 5, the care responsibility scores for the primary care physician, cardiologist 1, and cardiologist 2 would be compared to determine whether the patient is attributed to cardiologist 1 or cardiologist 2, and the patient-attribution assignment record may be created based on the comparison. The scores of clinicians with different clinician types (such as different specialties) may be compared to each other in some aspects. Accordingly, the care responsibilities scores of the primary care physician (as determined by curve 410) may be compared to the scores for cardiologist 1 (as determined by curve 420) and cardiologist 2 (as determined by curve 430). The clinicians may be ranked based on the care responsibility scores. In exemplary aspects, the patient-attribution assignment record assigns the highest ranked clinician(s) to the patient. In some embodiments, the patient is attributed to only one clinician, but it is also contemplated that patient-attribution assignment records for a particular patient may be created to assign the patient to multiple clinicians, such as the top two or top three ranked clinicians.

In some aspects, the patient may be attributed to the top ranking clinician(s) according to clinician type. For instance, the patient may be attributed to one clinician in each of the clinician types represented by the clinicians who interacted with the patient. Accordingly, in the example in FIG. 5, the patient may be attributed to the primary care physician and to one of the cardiologists. In this case, the care responsibility scores for the cardiologists may be compared to one another, and the patient may be attributed to the cardiologist with the highest score.

Further, assigning patients may also comprise comparing the care responsibility scores to a threshold score and determining that the clinician's score satisfies the threshold. Specifically, in some embodiments, the care responsibility score must meet or exceed a minimum threshold score in order for the patient to be attributed to the clinician. The threshold may be pre-determined or may be context dependent. In an example embodiment, a pre-determined threshold score of 0.05 is used, and clinicians with a care responsibility score less than 0.05 are not considered for a patient-attribution assignment.

Figure 6:
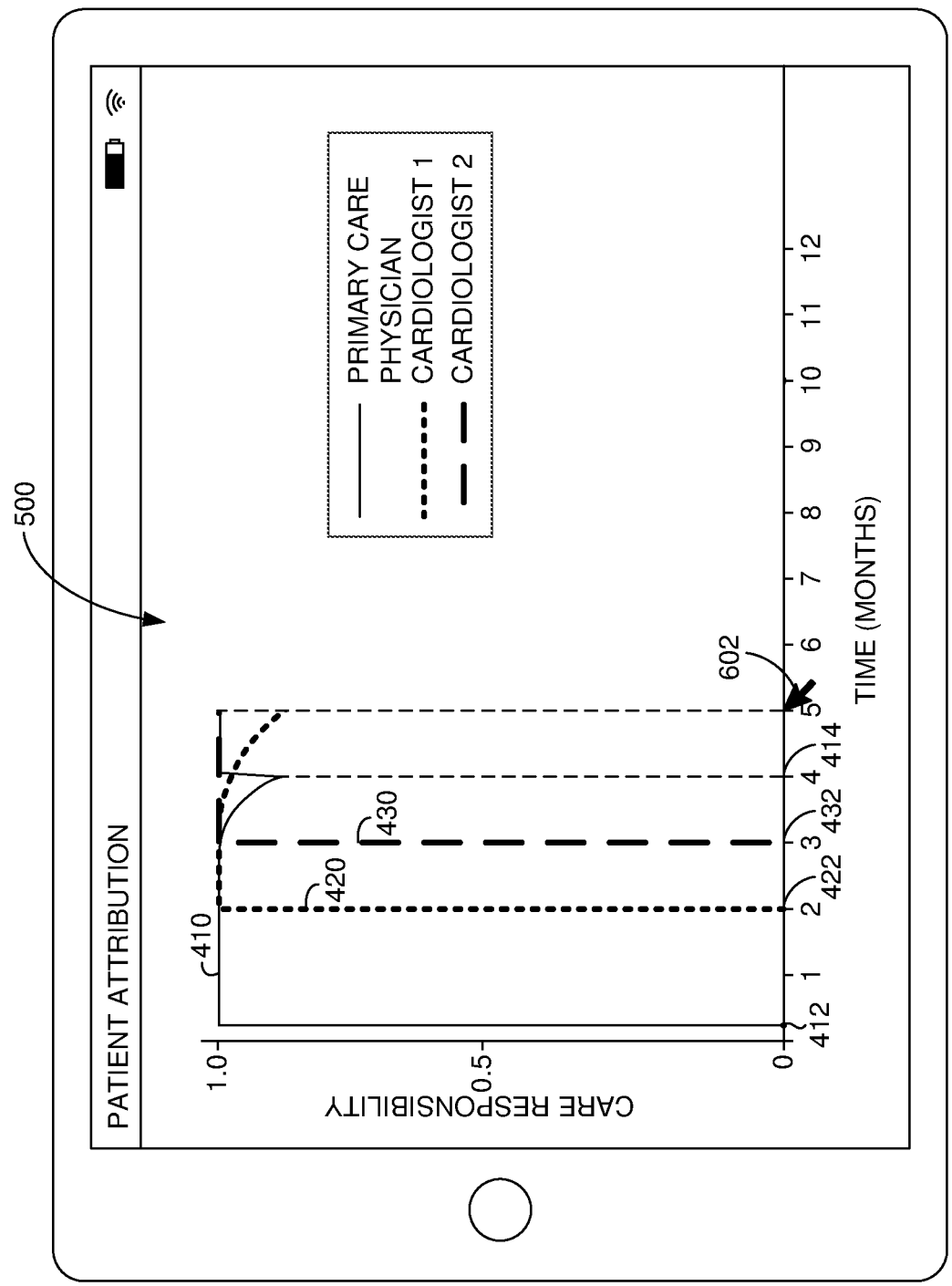
FIG. 6 depicts the user interface of FIG. 5 with the care responsibility curves as viewed before completion of a set time period, in accordance with an embodiment of the disclosure.

The curves in FIGS. 4-5 are shown over a pre-determined period of time. In some instances, the pre-determined time period is a set duration of time. For instance, the duration of time may be set to 12 months such that care responsibility curves may be patient-attribution assignment records determined from interactions over any twelve month period once a start date (or stop date) for the period is indicated. In exemplary embodiments, however, the pre-determined time period may have a pre-determined start date (such as the beginning of the current calendar or fiscal year) and may end on the current date or the most recent date from which data has been received. For instance, in some aspects, attributions at the end of a calendar year are used in evaluating the clinicians such that the attribution used for evaluating is based on a 12-month time period. However, it may be desirable for users to track attribution throughout the year. Accordingly, a user may check the attribution on May 1st, when the period began on January 1$^{st}$. FIG. 6 depicts user interface 500 upon selection of an earlier point in time. For instance, as indicated by cursor 602, a user may select the earlier time, such as May 1$^{st}$, such that the interface 500 includes care responsibility curves for the three clinicians in the example from FIG. 5 as the curves would exist on May 1$^{st}$. Care responsibility scores and attribution assignments may be determined based on the curves during this five month period. In this way, clinicians' responsibility levels may be monitored on a real-time basis. In some instances, the attribution assignments prior to the end of a pre-determined time frame (such as the end of a calendar or fiscal year) may be considered a preliminary assignment because attributions may change throughout the rest of the time period. Regardless of whether the assignments are preliminary or not, the assignments may be used to determine which clinicians are most responsible for the patient and, in some aspects, for taking an action.

Although FIGS. 3-6 illustrate phase transition curves with the decay being from 1 to 0, it is contemplated that different functions producing different types of curves capable of decaying to 0 may be used. In other embodiments, the curve may be a linear curve, a step-function curve, or a Heaviside function curve in which the curve immediately drops off at a point in time. In some aspects, multiple functions may be used for different clinicians or may be used in conjunction with one another for the same clinician.

Figure 7:
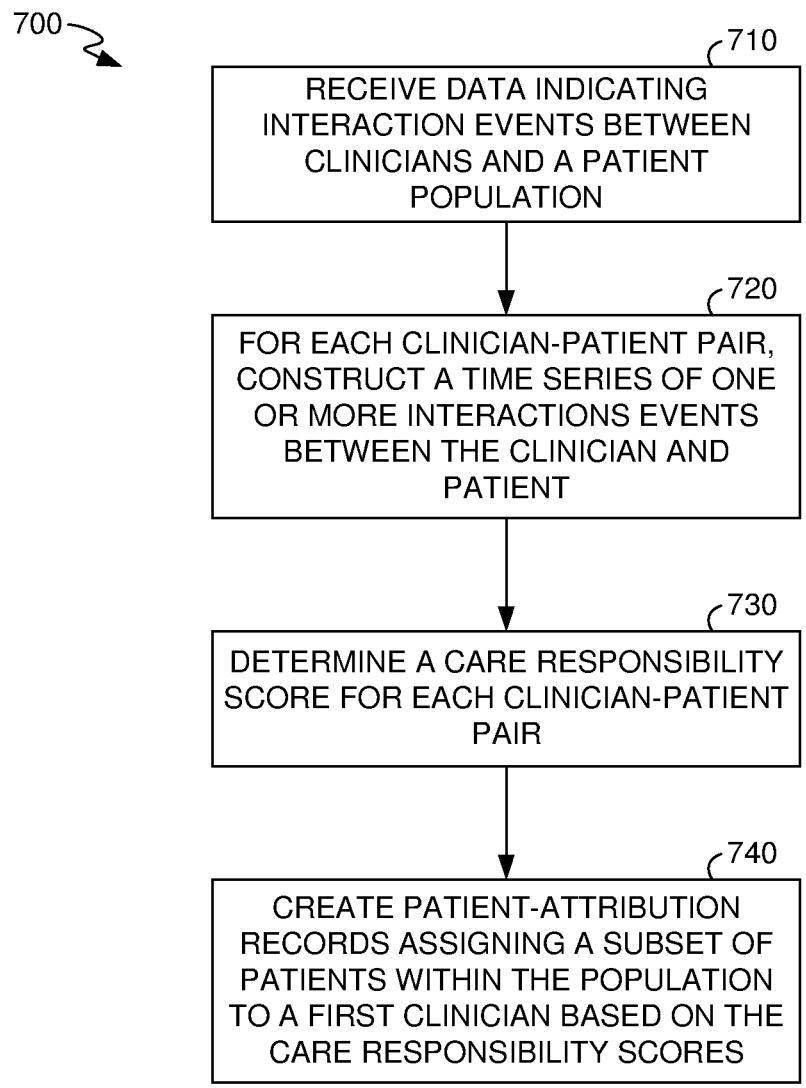
FIG. 7 depicts a flow diagram of a method for providing a decision support system for attributing a subset of patients within a population to a particular clinician, in accordance with an embodiment of the disclosure.

While only a single patient has been described with respect to FIGS. 4-6, patient attribution may done on a population of patients and multiple patients may be attributed to the same clinician. FIG. 7 provides a flow diagram illustrating a method 700 for attributing a subset of a population of patients to a clinician. Just as with method 200, interaction events indicating interactions between clinicians and patients are identified, at step 710. The patients comprise a population of patients with at least one commonality. The commonality may be a clinical condition, healthcare facility, insurance provider, geographical region, or demographic information. The number of interactions and clinicians with whom the patient interacted may vary across the population. At step 720, a time series of the interactions may be constructed for each patient-clinician pair with each time series indicating interactions between one particular clinician and one particular patient within the population of patients. Care responsibility curves may be generated based on the time series and a determined rate of decay of the care responsibility levels set for each interaction. Just as with method 200 of FIG. 2, the rate of decay may be specific to the interaction type and clinician type.

At step 730, a care responsibility score is determined for each clinician-patient combination, and a subset of patients within the population may be assigned to a clinician based on the care responsibility scores, at step 740. The assignments may be made based on a comparison of care responsibility scores for clinicians who interacted with a particular patient. The clinician may be assigned patients for whom the clinician has the highest care responsibility score, either overall or by clinician type, relative to other clinicians who interacted with the same patient.

Figure 8A:
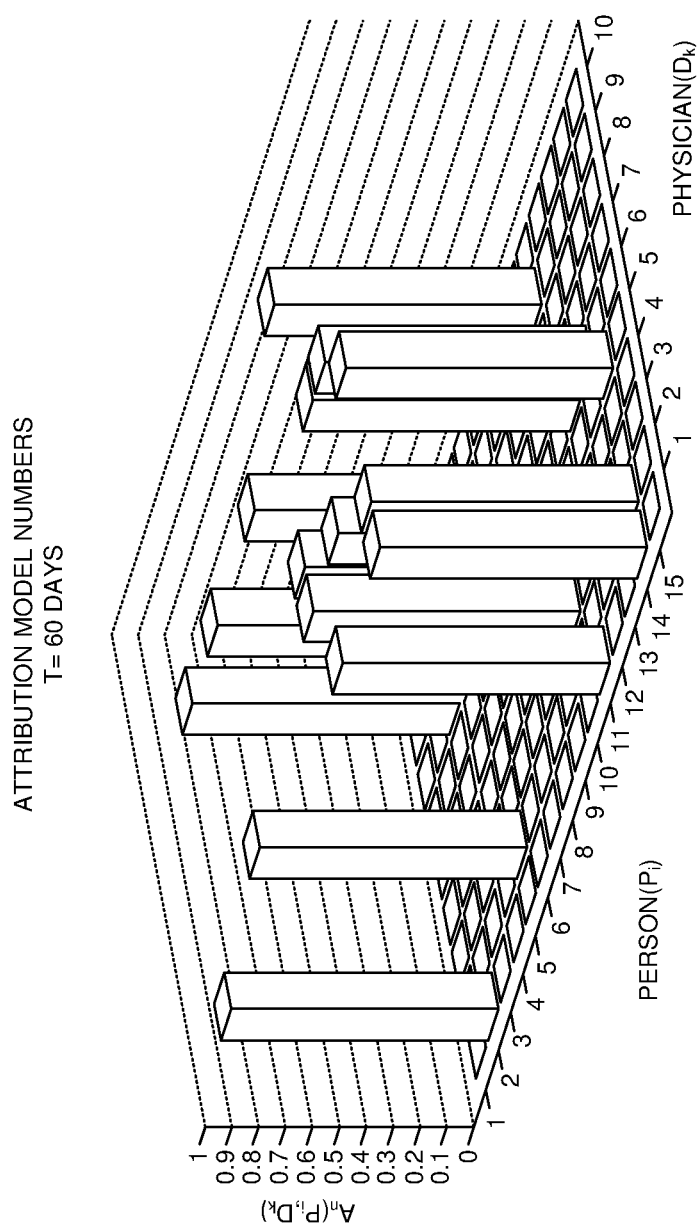
FIG. 8A-C depict graphical representations of the care responsibility scores for a group of potentially responsible clinicians, in accordance with an embodiment of the disclosure.
Figure 8B:
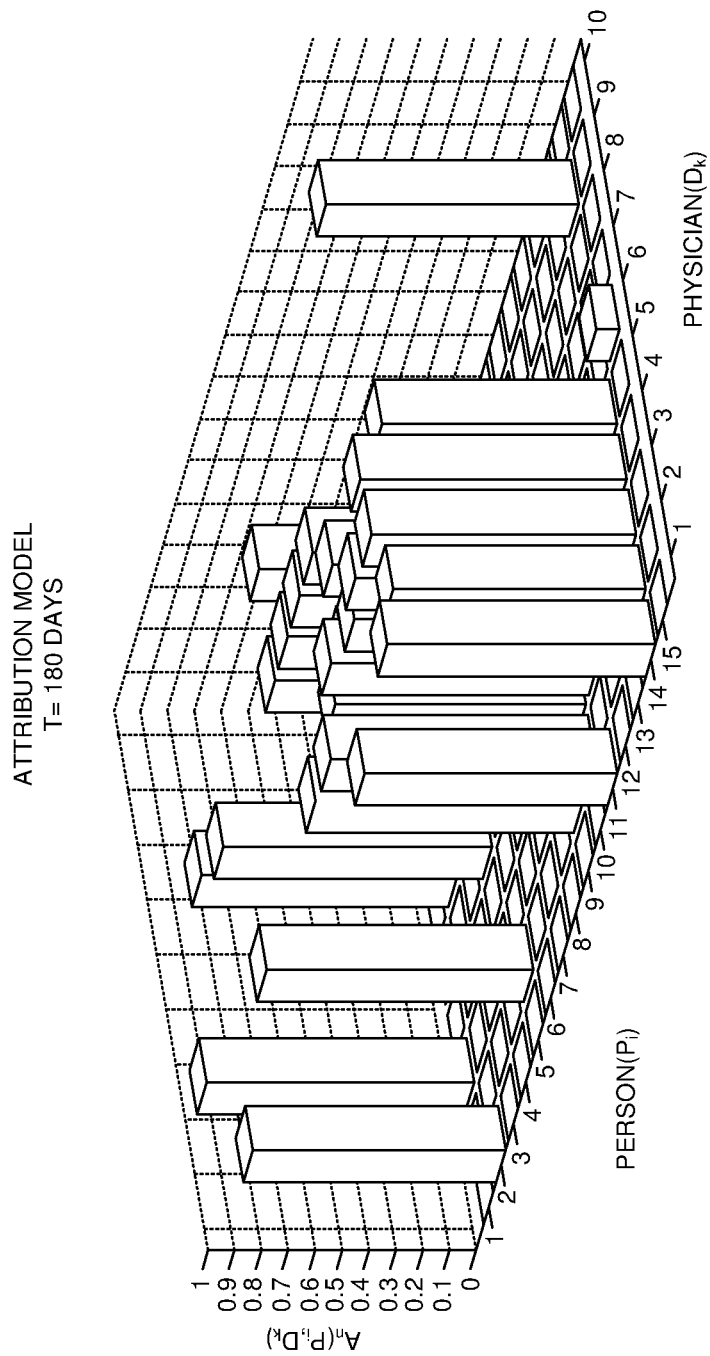
Figure 8C:
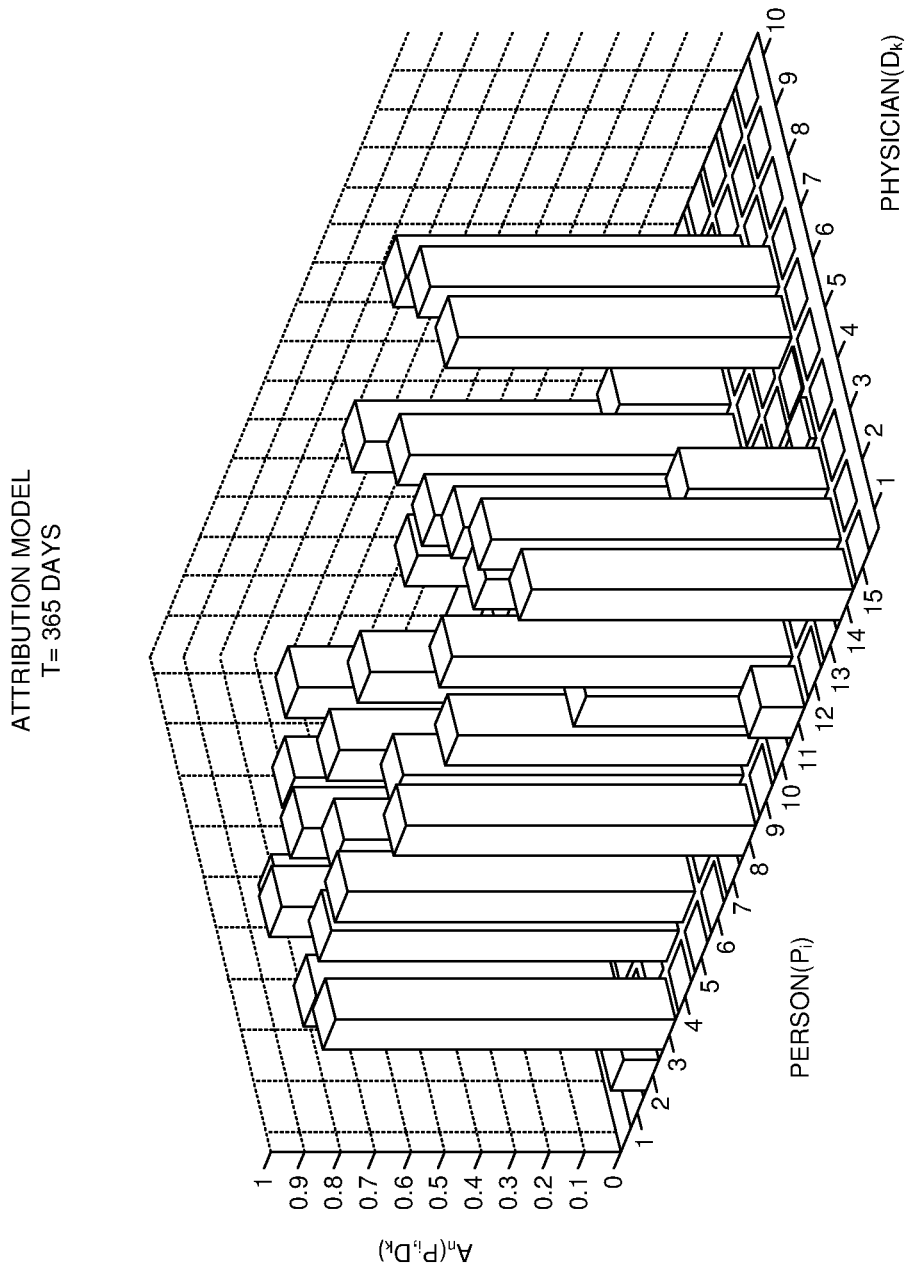

Turning to FIGS. 8A-8C, graphical illustrations of physicians' care responsibility scores for a population of patients in an embodiment reduced to practice are depicted. FIG. 8A indicates the care responsibility scores after a time period of 60 days, while FIGS. 8B and 8C depict the scores after time periods of 180 days and 360 days, respectively. As illustrated, there is a trend for more interactions to occur as time progresses; however, the care responsibility score for a given clinician-patient pair can change, such as by increasing or decreasing, based on the decay of the care responsibility level from prior interactions.

In accordance with some embodiments of the present disclosure, a user may be presented with a graphic user interface providing the current patients attributed to the clinician, the care responsibilities levels for the clinician, and/or the clinician's care responsibility curve generated for one or more patients with whom the clinician interacted. In some aspects, information pertaining to multiple clinicians may be provided for display within the graphic user interface. For instance, care responsibility curves for all clinicians interacting with patient or a set of patients may be displayed as shown in user interface 500 of FIGS. 5-6, or graphical representations of the care responsibility scores for a population of patients may be provided, such as in FIGS. 8A-8C.

As described, embodiments of the disclosure may track clinicians' interactions with patients to create patient-attribution assignment records that accurately reflect the clinicians' involvement with and responsibility over the care of one or more patients. This patient-attribution assignment may be used to determine responsible clinicians to contact, such as in emergency situations for instance. In some aspects, clinicians to whom a patient is attributed may be automatically notified if there is an emergency care event. The notification may be provided via a user/clinician interface, such as interface 142, described in connection with FIG. 1A. The patient-attribution assignments may also be used to identify a responsible clinician to contact in non-emergency situations for questions or concerns about a patient's clinical condition or care options, for example.

Further, patient-attribution assignments may be used by clinicians so that a clinician can better manage the care to the patients for which the clinician is responsible. For instance, clinicians may desire to ensure that patients for which they are responsible are meeting certain preventive or therapeutic care requirements. In an example embodiment, a clinician utilizes the patient-attribution assignments to determine that a population of diabetic patients attributed to the clinician have had blood sugar level testing performed within a certain time period, such as six months. Additionally, for example, a clinician may use the assignments to determine that a population of heart-failure patients attributed to the clinician have up-to-date cholesterol medications. In other words, a population or subset of population of patients with a common clinical condition may be attributed to a particular clinician, and the attribution assignments may be used to identify whether each patient within the subset has met care requirements for the clinical condition and subsequently notify the clinician of any patient who has not met the care requirements. In this way, these assignments are used to ensure that at least one clinician is identified as being responsible for a particular patient's care, thereby increasing the quality of care to that patient, and the disclosed methods and systems of attributing patients provides a more accurate assignment for ensuring quality care.

Some embodiments of the disclosure further comprise using the patient-attribution assignments to evaluate clinicians. For instance, the outcomes for the patient(s) attributed to a particular clinician may be received and used to evaluate the clinicians. Evaluations of a clinician may include scoring a clinician or categorizing the clinician based on patient outcomes. Additionally, in some aspects, the care costs for the patient(s) attributed to the particular clinician may be received and used to evaluate the clinicians as an indicator of efficiency or for pay-for-performance incentives. In some instances, the outcome and the care costs are used in conjunction with one another to evaluate a clinician or group of clinicians. Additionally, in some embodiments, a risk level or risk index may be received for each particular patient, and the risk levels of a subset of patients attributed to a particular clinician may determine a panel weight. The panel weight may be used in comparing the outcomes and care costs associated with each clinician. In the context of an ACO, for instance, clinicians may receive incentives for good outcomes and low care costs, but by using a panel weight, the outcomes and costs for clinicians assigned to higher risk patients are not directly compared to outcomes and costs for clinicians with lower risk patients. Because the present disclosure allows tracking of patient-attribution assignments in real time, the evaluations can further be provided in real time rather than being provided retrospectively at the end of a time period.

Further, embodiments of the disclosure may be used as a learning tool to optimize patient-attribution assignments. For instance, embodiments may associate a patient's outcome with the patient-attribution assignment and utilize that information to determine which clinicians have patient attributions in which the patient is associated with better patient outcomes. Additionally, the optimal number or frequency of interactions with a patient may be learned based on patient outcomes. Such learning techniques may involve using one or more machine-learning models. Understanding the interactions and/or patient-attribution assignments that are associated with better patient outcomes may lead to improved results for patients in the future.

Further embodiments of this disclosure include creating an improved graphic user interface for patient attributions. In some aspects, the user interfaces is created for use by a patient or a clinician. For instance, in an example embodiment, a plurality of patient-attribution records are used to generate a user interface for a display component of a user device. The patient-attribution records may assign a particular clinician, such as a first clinician, to a particular patient based on a care responsibility score indicating a level of responsibility of the first clinician for the patient. The care responsibility scores and patient-attribution records are each determined as discussed with respect to method 200 of FIG. 2. The graphic user interface generated using the patient-attribution assignment records may include one or more user interface elements visually indicating one or more care responsibility scores for a particular clinician. An example graphic user interface includes user interface 400 of FIG. 4.

The one or more user interface elements may include a graphic depiction of the care contribution curves as shown in FIG. 4. The user interface elements may also include a time associated with interaction events and/or a time period associated with the care contribution scores. For example, the user interface elements may include a timeline of interactions between a particular clinician and a patient. The user interface may further include user interface elements to depict interactions between other clinicians and/or other patients as shown in FIGS. 5 and 6 for example. Additionally, the user interface elements, such as care contribution curves, may be updated as additional interaction events occur or as time passes, which effects the care contribution levels. In this way, the graphic user interface generated in accordance with embodiments of this disclosure includes a visual depiction of the patient-attribution assignment records to provide this information to a user in an easy-to-digest manner and using a limited amount of screen space. Such user interfaces providing accurate and up-to-date attribution information could not be generated using conventional methods of attributing patients to clinicians.

In some embodiments, a graphic user interface may be generated for display on a user device based on patient-attribution records created by or stored on a remote computing device. As such, one embodiment includes a computer system with one or more processors and one or more computer-storage media having instructions that, when executed by the one or more processors, cause a method to be performed. The method may include determining a plurality of interaction events between a plurality of patients and a plurality of clinicians where each interaction event is associated with one patient and one clinician and includes a time an interaction occurred. For each patient who interacted with a first clinician, a care responsibility score is determined for the first clinician. Determining the care responsibility score includes assigning an initial care responsibility level for each interaction event between the patient and the first clinician and determining a rate of decay of the care responsibility level for each interaction event between the patient and the first clinician. The initial care responsibility level and the rate of decay for each interaction event are used to determine the care responsibility score for the first clinician. Based on the care responsibility scores for each patient with whom the first clinician interacted, patient-attribution assignment records may be created to attribute one or more patients to the first clinician. Based on one or more patient attribution assignment records, a graphic user interface may be caused to be generated for display on a remote user device. The graphic user interface may include at least one or more user interface elements visually depicting at least some of the care responsibility scores. The one or more user interface elements may further identify particular patients within a population of patients or indicate a volume of patients who are attributed to the first clinician.

While a graphic user interface may be generated to indicate attributions of multiple patients to a particular clinician, other graphic user interfaces may be generated to visually depict relative care responsibility scores of multiple clinicians for a single patient. Accordingly, an example embodiment includes a computer system comprising a display component, one or more processors, and one or more computer-storage media having instructions that, when executed by the one or more processors, cause a method to be performed for generating a user interface based on patient-attribution assignment records. In accordance with the method, a plurality of care responsibility scores for a patient may be received. These scores may be received from a remote server and may be determined as described with respect to FIG. 2. Each care responsibility score may be associated with a particular clinician and indicate a level of clinician responsibility for the patient by the particular clinician. The care responsibility scores determined for the patient may be used to generate a graphic user interface for the display component of the computer system. The graphic user interface may be generated to include one or more interface elements indicating relative responsibility of each clinician over the patient. For instance, graphic user interface 500 of FIG. 5 includes one or more care responsibility curves for different physicians who interacted with a particular patient. The graphic user interface may be used to quickly ascertain the responsibility levels of different clinicians over time and the basis for the patient-attribution assignment record attributing the patient to one of the clinicians.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. Computer storage media having computer-executable instructions embodied thereon that, when executed, provide a decision support system and cause a processor to perform actions comprising:

for a selected patient, retrieving electronic medical records from different data sources where the electronic medical records include patient data stored in different formats;
extracting a set of data from the electronic medical records and mapping the set of data to a standard format;
identifying from the set of data in the standard format, in real-time, a plurality of interaction events between the patient and a plurality of clinicians based on the electronic medical records, wherein each interaction event including at least a time an interaction occurred;
constructing a time series of interactions between the patient and each clinician of the plurality of clinicians;
assigning an initial care responsibility level for each interaction within the time series;
determining a rate of decay of the care responsibility level for each interaction;
determining a care responsibility score for each clinician using the time series and the rate of decay for each interaction;
creating a patient-attribution assignment record attributing the patient to a group of clinicians from the plurality of clinicians based on the care responsibility score of each clinician, the patient-attribution assignment record based on a comparison of care responsibility scores for the plurality of clinicians who interacted with the patient;
storing the patient-attribution assignment record in a database that is accessible via a network; and
in response to a clinical event associated with the patient being detected in a computing system, transmitting a notification over a network in real-time to all clinicians in the group of clinicians to automatically notify the group of clinicians of the clinical event, wherein the transmitting is based on the patient-attribution assignment record of the patient.

2. The media of claim 1, wherein each interaction event indicates a type of interaction, and wherein the rate of decay for each interaction is based on the type of interaction and a clinician type.

3. The media of claim 2, wherein the type of interaction action includes one of an office visit, an examination, a consultation, a procedure, a consultation, or a referral.

4. The media of claim 1, wherein the computer-executable instructions for determining the care responsibility score further comprises instructions for creating one or more care responsibility curves for one or more clinicians from the plurality of clinicians, each care responsibility curve indicating care responsibility levels over time.

5. The media of claim 4, wherein the initial care responsibility level assigned to each interaction is a maximum level indicating full responsibility, and wherein the care responsibility levels over the one or more care responsibility curves are less than or equal to the maximum level and greater than or equal to a minimum level indicating no responsibility.

6. The media of claim 4, wherein the computer-executable instructions further comprise instructions for receiving a current time, and wherein the care responsibility score comprises an area under the one or more care responsibility curves over a period of time ending with the current time.

7. The media of claim 1, wherein the rate of decay for each interaction includes a period of time after the interaction until the care responsibility level begins to decay and a period of time over which decay occurs.

8. The media of claim 1, wherein the method the computer-executable instructions further comprise instructions for, based on the patient-attribution assignment record, notifying a first clinician from the group of clinicians of the clinical event associated with the patient.

9. A computer system comprising:
a display component;
one or more processors; and
one or more computer-storage media having instructions that, when executed by the one or more processors, cause a method to be performed, the method comprising:
for a selected patient, retrieving electronic medical records from different data sources where the electronic medical records include patient data stored in different formats;
extracting a set of data from the electronic medical records and mapping the set of data to a standard format;
generating from the set of data in the standard format, in real-time, a plurality of patient-attribution assignment records for each clinician of a plurality of clinicians, wherein a patient-attribution assignment record of the plurality of patient-attribution assignment records attributes a patient to a set of clinicians from the plurality of clinicians based on a care responsibility score indicating a level of responsibility of each clinician in the set of clinicians for the patient, wherein each care responsibility score for a given clinician is determined by:
assigning an initial care responsibility level for each interaction between the patient and the given clinician;
determining a rate of decay of the care responsibility level for each interaction; and
using the initial care responsibility level and the rate of decay for each interaction to determine the care responsibility score for the given clinician and updating the corresponding patient-attribution assignment record with the care responsibility score; and
storing the plurality of patient-attribution assignment records in a database that is accessible via a network;
in response to a clinical event associated with the patient being detected in a computing system, transmitting a notification over a network in real-time to all clinicians in the set of clinicians to automatically notify the set of clinicians of the clinical event, wherein the transmitting is based on the patient-attribution assignment record that identifies the set of clinicians attributed to the patient; and
dynamically updating the care responsibility score for a first clinician from the set of clinicians upon determining a subsequent interaction between the first clinician and the patient has occurred, and wherein one or more user interface elements associated with the patient is automatically updated based on updating the care responsibility score.

10. The system of claim 9, wherein the one or more user interface elements further indicate a time period associated with the one or more care responsibility scores.

11. The system of claim 10, wherein the one or more user interface elements includes a timeline of interactions between the first clinician and one or more patients.

12. The system of claim 9, wherein the computer-storage media further comprises instructions for updating the care responsibility score for the first clinician upon determining a subsequent interaction between the first clinician and a first patient has occurred, and wherein a first user interface element associated with the first patient is automatically updated based on updating the first care responsibility score.

13. The system of claim 9, wherein the one or more user interface elements comprises a care responsibility curve determined using the rate of decay and a phase transition function.

14. A computerized method for a decision support system, the method executed by one or more processors and the method comprising:
    retrieving electronic medical records from different data sources where the electronic medical records include patient data stored in different formats;
    extracting a set of data from the electronic medical records and mapping the set of data to a standard format, wherein the set of data includes a clinical care data for a population of patients;
    receiving, in real-time, a set of clinical care data for the population of patients, the clinical care data including a plurality of interaction events between at least one patient within the population and each clinician of a plurality of clinicians;
    for each patient-clinician pair, constructing a time series of interactions over a period of time based on the plurality of interaction events;
    for each patient-clinician pair, determining a care responsibility score measuring an amount of responsibility the clinician is considered to have for the patient, the care responsibility score being determined by:
        assigning an initial care responsibility level for each interaction within the time series,
        determining a rate of decay of the initial care responsibility level for each interaction,
        creating a care responsibility curve based on the initial care responsibility level and the rate of decay, and
        determining an area under the care responsibility curve;
    creating patient-attribution assignment records assigning a subset of patients within the population of patients to a set of clinicians from the plurality of clinicians, wherein the set of clinicians have higher care responsibility scores for the subset of patients relative to one or more additional clinicians within the plurality of clinicians;
    storing the patient-attribution assignment records in a database that is accessible via a network;
    in response to a clinical event associated with a first patient from the sub-set of patients being detected in a computing system, transmitting a notification over a network in real-time to all clinicians in the set of clinicians to automatically notify the set of clinicians of the clinical event, wherein the transmitting is based on the patient-attribution assignment record that identifies the set of clinicians attributed to the first patient; and
    receiving additional data indicating one or more additional interaction events between at least one patient within the subset and at least one clinician within the one or more additional clinicians; and
    dynamically updating one or more patient-attribution assignment records to reassign the at least one patient within the subset of patients to a different clinician based on the one or more additional interaction events.

15. The computerized method of claim 14, wherein the population of patients is defined by a commonality of at least one of a geographic area, a health care facility, an insurance provider, or a clinical condition.

16. The computerized method of claim 15, wherein the commonality defining the population of patients is a clinician condition, and wherein the method further comprises, based on assigning the subset of patients to the set of clinicians, identifying whether each patient within the subset has met care requirements for the clinical condition and notifying the set of clinicians of any patient who has not met the care requirements.

17. The computerized method of claim 14 further comprising receiving additional data indicating one or more additional interaction events between at least one patient within the subset and at least one clinician within the one or more additional clinicians.

18. The computerized method of claim 17 further comprising updating one or more patient-attribution assignment records to reassign at least one patient within the subset of patients to a different clinician based on the one or more additional interaction events.

19. The computerized method of claim 14 further comprising evaluating a first clinician from the set of clinicians based on outcomes and health costs of the subset of patients.

20. The computerized method of claim 14 further comprising:
    determining a risk level of each patient within the subset of patients that are assigned to a first clinician;
    determining a panel weight for the subset of patients based on the risk level; and
    using the panel weight in evaluating the first clinician.

* * * * *